(12) United States Patent
Commereuc et al.

(10) Patent No.: US 7,696,397 B2
(45) Date of Patent: Apr. 13, 2010

(54) CATALYTIC COMPOSITION AND ITS APPLICATION TO OLEFIN OLIGOMERIZATION

(75) Inventors: Dominique Commereuc, Meudon (FR); Alain Forestiere, Vernaison (FR); François Hugues, Vernaison (FR); Hélène Olivier, Rueil-Malmaison (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 143 days.

(21) Appl. No.: 11/767,164

(22) Filed: Jun. 22, 2007

(65) Prior Publication Data
US 2008/0033224 A1    Feb. 7, 2008

Related U.S. Application Data

(60) Division of application No. 11/107,794, filed on Apr. 18, 2005, now Pat. No. 7,235,703, which is a continuation of application No. 09/580,179, filed on May 26, 2000, now abandoned.

(30) Foreign Application Priority Data
May 27, 1999    (FR)    ................... 99 06749

(51) Int. Cl.
*C07C 2/02*    (2006.01)
*B01J 31/00*   (2006.01)

(52) U.S. Cl. .............. 585/522; 585/521; 585/532; 502/103; 502/118

(58) Field of Classification Search ............. 502/103, 502/118; 585/521, 522, 532
See application file for complete search history.

(56) References Cited

U.S. PATENT DOCUMENTS

| 3,755,283 A | 8/1973 | Yamawaki et al. |
| 3,992,323 A | 11/1976 | Yoo et al. |
| 4,283,305 A | 8/1981 | Chauvin et al. |
| 4,316,851 A | 2/1982 | Le Pennec et al. |
| 4,362,650 A | 12/1982 | Chauvin et al. |
| 4,366,087 A | 12/1982 | Le Pennec et al. |
| 4,398,049 A | 8/1983 | Le Pennec et al. |
| 4,476,341 A | 10/1984 | Mathys |
| 4,538,018 A | 8/1985 | Carter |
| 4,551,438 A | 11/1985 | Miller |
| 4,709,112 A | 11/1987 | Sato et al. |
| 4,716,239 A | 12/1987 | Provin et al. |
| 4,935,575 A | 6/1990 | Frame |
| 5,037,788 A | 8/1991 | Frame |
| 5,059,571 A | 10/1991 | Chauvin et al. |
| 5,231,065 A | 7/1993 | Hawley et al. |
| 5,345,023 A | 9/1994 | Chauvin et al. |
| 5,496,783 A | 3/1996 | Chauvin et al. |
| 5,502,018 A | 3/1996 | Chauvin et al. |
| 5,536,689 A | 7/1996 | Chauvin et al. |
| 5,550,304 A | 8/1996 | Chauvin et al. |
| 5,550,306 A | 8/1996 | Chauvin et al. |
| 5,596,053 A | 1/1997 | Kang et al. |
| 5,633,418 A | 5/1997 | Sato et al. |
| 5,744,678 A | 4/1998 | Aida et al. |
| 6,251,817 B1 * | 6/2001 | Erickson et al. ............ 502/152 |
| 6,444,866 B1 | 9/2002 | Commereuc et al. |
| 6,468,948 B1 | 10/2002 | Rossi et al. |
| 6,501,001 B2 | 12/2002 | Commereuc et al. |
| 6,573,414 B2 | 6/2003 | McAtee et al. |
| 6,667,269 B2 | 12/2003 | Oliver-Bourbigou et al. |
| 6,706,657 B2 | 3/2004 | Commereuc et al. |
| 6,911,410 B2 | 6/2005 | Lecocq et al. |

FOREIGN PATENT DOCUMENTS

EP    0 012 685    6/1980

* cited by examiner

*Primary Examiner*—In Suk Bullock
(74) *Attorney, Agent, or Firm*—Millen, White, Zelano, Branigan, P.C.

(57) ABSTRACT

An improved catalytic composition for oligomerization, in particular dimerization, of monoolefins comprises the product resulting from bringing the following three constituents into contact in any order:
a) at least one divalent nickel compound;
b) at least one hydrocarbylaluminium dihalide, optionally enriched with an aluminum trihalide; and
c) at least one organic Bronsted acid;

the catalytic composition being pre-conditioned in a solvent before using it for oligomerization.

15 Claims, No Drawings

CATALYTIC COMPOSITION AND ITS APPLICATION TO OLEFIN OLIGOMERIZATION

This application is a divisional of U.S. Ser. No. 11/107,794, filed Apr. 18, 2005, now U.S. Pat. No. 7,235,703, which is a continuation of U.S. Ser. No. 09/580,179, filed May 26, 2000, now abandoned, each of which is incorporated by reference herein.

FIELD OF THE INVENTION

The present invention relates to a novel catalytic composition for use in oligomerization processes, in particular for monoolefin dimerization.

It also relates to a process for oligomerization, in particular dimerization, of monoolefins, using such a catalytic composition.

DESCRIPTION OF THE PRIOR ART

The preparation of catalysts for dimerization or co-dimerization of monoolefins such as ethylene, propylene, butenes or pentenes is known. Examples of such catalysts which can be cited are the products of the interaction of π-allyl nickel phosphine halides with Lewis acids (French patent FR-B-1 410 430), the products of the interaction of nickel phosphine halides with Lewis acids (U.S. Pat. No. 3,485,881) and the products of the interaction of certain nickel carboxylates with hydrocarbylaluminium halides (U.S. Pat. No. 3,321,546).

Almost all of those catalysts use a ligand such as an organic phosphorus compound and it is preferable to have phosphorus-free oligomerization catalysts available. To this end, it is possible to use zerovalent nickel compounds but they are of little practical use because of their instability. It is also possible to use catalysts in which the nickel is deposited on a mineral support comprising acid sites, such as silica, alumina or silica-aluminas. However, in that case the catalysts are solid, in contrast to the desired liquid catalysts.

U.S. Pat. No. 4,283,305 teaches that an association of a divalent nickel compound, a hydrocarbyl-aluminium halide with formula $AlR_mX_{3-m}$ where R is a hydrocarbyl radical containing 1 to 12 carbon atoms, X is a chlorine or bromine atom, and m is a number from 1 to 2, and a compound with a Bronsted acid nature, leads to a catalytic composition that is more active than previously, and also less sensitive to the trace impurities which are routinely found in industrial olefinic feeds.

SUMMARY OF THE INVENTION

It has now, unexpectedly, been found that for a catalytic composition obtained by bringing a divalent nickel compound into contact with an organic Bronsted acid and a hydrocarbylaluminium dihalide, pre-conditioning the catalytic composition in a solvent before using it for oligomerization can still further increase the activity for olefin oligomerization. The use of a hydrocarbylaluminium dihalide enriched with an aluminium trihalide can still further increase the activity of the catalytic composition.

DETAILED DESCRIPTION OF THE INVENTION

More precisely, said improved catalytic composition comprises the product resulting from bringing the following three constituents into contact in any order:

a) at least one divalent nickel compound;
b) at least one hydrocarbylaluminium dihalide with formula $AlRX_2$, where R is a hydrocarbyl radical containing 1 to 12 carbon atoms such as alkyl, aryl, aralkyl or cycloalkyl, and X is a chlorine or bromine atom; and
c) at least one organic Bronsted acid;

the mixture obtained being pre-conditioned in a solvent, at a controlled temperature and for a pre-set period, prior to its use.

The divalent nickel compound can be any compound soluble in a proportion of more than 1 g per litre in a hydrocarbon medium, more particular in the reactants and the reaction medium. Preferably, nickel carboxylates are used with general formula $(R_1COO)_2Ni$, where $R_1$ is a hydrocarbyl radical, for example alkyl, cycloalkyl, alkenyl, aryl, aralkyl or alkaryl, containing up to 20 carbon atoms, preferably a hydrocarbyl residue containing 5 to 20 carbon atoms. Radical $R_1$ can be substituted by one or more halogen atoms, hydroxyl groups, ketone, nitro, cyano or other groups that do not interfere with the reaction. The two radicals $R_1$ can also constitute an alkylene residue containing 6 to 18 carbon atoms. Non limiting examples of nickel compounds are the following divalent nickel salts: octoate, 2-ethylhexanoate, decanoate, stearate, oleate, salicylate and hydroxydecanoate. Preferably, nickel 2-ethylhexanoate is used.

The Bronsted acid compound has formula HY, where Y is an organic anion, for example carboxylic, sulphonic or phenolic. Preferably, acids with a $pK_a$ of a maximum of 3 at 20° C. are used, more particularly those which are soluble in the nickel compound or in its solution in a hydrocarbon or another suitable solvent. One preferred class of acids comprises the group formed by halogenocarboxylic compounds with formula $R_2COOH$ where $R_2$ is a halogenated alkyl radical, in particular those which contain at least one halogen atom alpha to the —COOH group, with a total or 2 to 10 carbon atoms. Preferably, a halogenoacetic acid with formula $CX_pH_{3-p}$—COOH is used where X is fluorine, chlorine, bromine or iodine, and p is a whole number from 1 to 3. Examples which can be cited are trifluoroacetic, difluoroacetic, fluoroacetic, trichloroacetic, dichloroacetic and chloroacetic acids. These examples are not limiting and it is also possible to use arylsulphonic acids, alkylsulphonic acids, fluoroalkylsulphonic acids, picric acid and nitroacetic acid. Preferably, trifluoroacetic acid is used.

The three constituents of the catalytic formula can be mixed in any order. However, it is preferable to first mixture the nickel compound with the organic Bronsted acid then to introduce the aluminium compound. The mole ratio of the hydrocarbylaluminium dihalide to the nickel compound, expressed as the Al/Ni ratio, is 2/1 to 50/1, preferably 2/1 to 20/1. The mole ratio of the Bronsted acid to the nickel compound is 0.25/1 to 10/1, preferably 0.25/1 to 5/1.

Pre-conditioning the catalytic composition consists of mixing the three constituents in a hydrocarbon solvent, for example in an alkane or in an aromatic hydrocarbon, or in a halogenated hydrocarbon or, as is preferred, in a mixture with a composition analogous to that of the mixtures obtained in the dimerization or oligomerization reaction itself. Thus for a catalytic composition intended for propylene dimerization, the pre-conditioning solvent can principally be constituted by isohexenes.

The mixture is generally produced by stirring in an inert atmosphere, for example in nitrogen or argon, at a controlled temperature of 0° C. to 80° C., preferably 10° C. to 60° C., for a period of 1 minute to 5 hours, preferably 5 minutes to 1 hour. The solution obtained is then transferred into the oligomerization reactor under an inert atmosphere.

In a preferred implementation, in the catalytic composition of the invention, the hydrocarbylaluminium dihalide can be enriched with an aluminium trihalide, the mixture of the two compounds then having formula $AlR_nX_{3-n}$, where R and X are as defined above and n is a number from 0 to 1 (limits excluded).

The hydrocarbylaluminium dihalide compounds enriched in aluminium trihalide are obtained by mixing a hydrocarbylaluminium dihalide with formula $AlRX_2$ where R is a hydrocarbyl radical containing 1 to 12 carbon atoms, such as alkyl, aryl, aralkyl, alkaryl or cycloalkyl and X is a chlorine atom or a bromine atom, with an aluminium trihalide $AlX_3$. Non limiting examples of such compounds which can be cited are: dichloroethylaluminium enriched with aluminium trichloride, the mixture having formula $AlEt_{0.9}Cl_{2.1}$, for example; dichloroisobutylaluminium enriched with aluminium trichloride, the mixture having formula $AlIBu_{0.9}Cl_{2.1}$, for example, and dibromoethylaluminium enriched with aluminium tribromide, the mixture having formula $AlEt_{0.9}Br_{2.1}$, for example.

In this case as well, the three constituents of the catalytic formula can be mixed in any order. It is also preferable to first mix the nickel compound with the organic Bronsted acid, then to introduce the aluminium compound. In this case, it is =the mole ratio between the hydrocarbylaluminium dihalide enriched with aluminium trihalide and the nickel compound, expressed as the Al/Ni ratio, which is 2/1 to 50/1, preferably 2/1 to 20/1. As indicated above, the mole ratio of the Bronsted acid to the nickel compound is still 0.25/1 to 10/1, preferably 0.25/1 to 5/1.

The invention also relates to a process for oligomerization, in particular dimerization, of monoolefins in the presence of the catalytic system defined above.

Examples of monoolefins that can be dimerized or oligomerized are ethylene, propylene, butenes, pentenes and hexenes, used pure or as a mixture, contained in cuts from refining or from chemistry. These olefins can also be co-oligomerized between themselves.

The process can be carried out in a reactor with one or more reaction stages in series, the olefinic feed and/or the previously pre-conditioned catalytic composition being introduced continuously, either to the first stage, or to the first and to any other stage.

The process is generally carried out at a temperature of −20° C. to +80° C., under pressure conditions such that at least the major portion of the reactants are maintained in the liquid phase or in the condensed phase.

At the reactor outlet, the catalyst can be deactivated, for example by injecting ammonia and/or an aqueous sodium hydroxide solution and/or an aqueous sulphuric acid solution. The unconverted olefins and alkanes which may be present in the feed are then separated from the oligomers by distillation.

The products obtained by the process of the invention can be used, for example, as constituents for automobile fuels and/or as feeds for a hydroformylation process for synthesising aldehydes and alcohols.

The entire disclosure of all applications, patents and publications, cited above and below, and of corresponding French application 99/06749, filed on May 27, 1999 are hereby incorporated by reference.

The following examples illustrate the invention without in any way limiting its scope.

EXAMPLE 1 (COMPARATIVE)

Preparation of Catalyst:
In this example of the prior art, the catalyst was prepared in situ in the autoclave where oligomerization took place, without pre-conditioning, and used dichloroethylaluminium as the aluminium compound.

Use in Oligomerization:
A solution of 0.043 g of nickel 2-ethylhexanoate containing 13% by weight of nickel in 40 ml of isohexene solvent was introduced into a 250 ml stainless steel autoclave provided with stirring and wherein the temperature could be regulated by circulating water in an external envelope, followed by 10 g of a mother liquor prepared from 0.11 g of trifluoroacetic acid made up to 100 g with isohexene solvent, introduced with stirring. Finally, a solution of 0.18 g of dichloroethylaluminium in 50 ml of isohexene solvent was injected. This corresponded to 1.41 mmole of aluminium and an Al/Ni mole ratio of 15/1.

Subsequently, 10 g of isohexenes was added to the autoclave to make up the solvent, followed by 10.8 g of liquid propylene via pressure lock. The temperature was rapidly raised to 40° C. After 15 minutes of reaction, the conversion of propylene into a mixture of dimers, trimers and tetramers containing 80% by weight of dimers was 67%.

EXAMPLE 2 (IN ACCORDANCE WITH THE INVENTION)

Preparation of Catalyst:
0.043 g of nickel 2-ethylhexanoate containing 13% by weight of nickel was introduced into a 250 ml glass flask provided with a magnetic stirrer, then the flask was carefully purged and placed under an argon atmosphere. A transfer needle was used to introduce 40 ml of a fraction of isohexenes distilled under argon and dried over 3A molecular sieve, which was then used as the solvent. Stirring dissolved the nickel salt. 10 g of a mother liquor prepared from 0.11 g of trifluoroacetic acid made up to 100 g with the isohexene solvent was then injected. This was all placed, with continued stirring, in a thermostatic bath regulated to 30° C.

A further flask purged with argon was used to prepare a solution of 0.18 g of dichloroethylaluminium in 50 ml of isohexene solvent. The solution obtained was slowly added to the nickel solution prepared above using a transfer needle. This corresponded to 1.41 mmole of total aluminium and to a Al/Ni mole ratio of 15/1. This was all pre-conditioned at 30° C. for 30 minutes with stirring.

Use in Oligomerization:
The pre-conditioned catalytic solution was transferred under argon to an autoclave as described in Example 1. 10 g of isohexenes was then introduced into the autoclave to make up the solvent, followed by 10.8 g of liquid propylene using a pressure lock. The temperature was rapidly raised to 40° C. The reaction was followed by periodically removing samples for gas chromatographic analysis. After 15 minutes of reaction, the conversion of propylene into a mixture of dimers, trimers and tetramers analogous to that of Example 1 was 86%.

EXAMPLE 3 (IN ACCORDANCE WITH THE INVENTION)

Preparation of Catalyst:
0.043 g of nickel 2-ethylhexanoate containing 13% by weight of nickel was introduced into a 250 ml glass flask provided with a magnetic stirrer, then the flask was carefully purged and placed under an argon atmosphere. A transfer needle was used to introduce 40 ml of a fraction of isohexenes distilled under argon and dried over 3A molecular sieve, which was then used as the solvent. Stirring dissolved the nickel salt. 10 g of a mother liquor prepared from 0.11 g of trifluoroacetic acid made up to 100 g with the isohexene solvent was then injected. This was all placed, with continued stirring, in a thermostatic bath regulated to 30° C.

50 ml of isohexene solvent was introduced into a further flask purged with argon, followed by 0.165 g of dichloroethylaluminium and finally 0.015 g of aluminium trichloride, corresponding to a compound with formula $AlEt_{0.92}Cl_{2.08}$. The solution obtained was slowly added to the nickel solution prepared above using a transfer needle, whereupon the colour changed from green to yellow. This corresponded to 1.41 mmole of total aluminium and to an Al/Ni mole ratio of 15/1. This was all pre-conditioned at 30° C. for 30 minutes with stirring.

Use in Oligomerization:

The pre-conditioned catalytic solution was transferred under argon to an autoclave as described in Example 1. 10 g of isohexenes was then introduced into the autoclave to make up the solvent, then 10.8 g of liquid propylene using a pressure lock. The temperature was rapidly raised to 40° C. The reaction was followed by periodically removing samples for gas chromatographic analysis. After 15 minutes of reaction, the conversion of propylene into a mixture of dimers, trimers and tetramers analogous to that of Example 1 was 89%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the production of a catalytic composition, comprising bringing the following three constituents into contact in any order:
   a) at least one divalent nickel compound;
   b) at least one hydrocarbylaluminium dihalide with formula $AlRX_2$, where R is a hydrocarbyl radical containing 1 to 12 carbon atoms and X is a chlorine or bromine atom; and
   c) at least one organic Bronsted acid;
   and preconditioning a mixture thus obtained in a solvent, at a controlled temperature and for a pre-set period, prior to its use.

2. A process according to claim 1, wherein said divalent nickel compound is a nickel carboxylate with the formula:

where $R_1$ is an alkyl, cycloalkyl, alkenyl, aryl, aralkyl or alkaryl radical containing up to 20 carbon atoms.

3. A process according to claim 1, wherein a $pK_a$ of said organic Bronsted acid is a maximum of 3 at 20° C. and said acid is a halogenocarboxylic compound with formula $R_2COOH$ where $R_2$ is a halogenated alkyl radical.

4. A process according to claim 1, wherein said organic Bronsted acid is a halogenoacetic acid with formula $CX_pH_{3-p}$—COOH where X is fluorine, chlorine, bromine or iodine, and p is a whole number from 1 to 3.

5. A process according to claim 1, wherein said organic Bronsted acid is trifluoroacetic acid, trichloroacetic acid or tribromoacetic acid.

6. A process for the production of a catalytic composition, comprising bringing the following three constituents into contact in any order:
   a) at least one divalent nickel compound;
   b) at least one hydrocarbylaluminium dihalide with formula $AlRX_2$, where R is a hydrocarbyl radical containing 1 to 12 carbon atoms, and X is a chlorine or bromine atom; and
   c) at least one organic Bronsted acid;
   and preconditioning a mixture thus obtained by mixing the three constituents in a hydrocarbon or halogenohydrocarbon solvent with stirring and in an inert atmosphere at a controlled temperature of 0° C. to 80° C. and for a duration of 1 minute to 5 hours.

7. A process according to claim 1, wherein the mole ratio of said hydrocarbylaluminium dihalide to said nickel compound, expressed as the Al/Ni ratio, is 2/1 to 50/1, and the mole ratio of said Bronsted acid to said nickel compound is 0.25/1 to 10/1.

8. A process according to claim 1, wherein said hydrocarbylaluminium dihalide is enriched with an aluminium trihalide, the mixture of these two compounds having formula $AlR_nX_{3-n}$, R and X being as defined in claim 1 and where n is a number between 0 and 1.

9. A process according to claim 8, wherein the mole ratio of hydrocarbylaluminium dihalide enriched with an aluminium trihalide and the nickel compound, expressed as the ratio Al/Ni, is 2/1 to 50/1, and the mole ratio of the Bronsted acid to the nickel compound is 0.25/1 to 10/1.

10. A process according to claim 8, wherein said hydrocarbylaluminium dihalide enriched with an aluminium trihalide is obtained by mixing a hydrocarbylaluminium dihalide with formula $AlRX_2$ with an aluminium trihalide AlX.

11. A process according to claim 8, wherein said hydrocarbylaluminium dihalide enriched with an aluminium trihalide is obtained by mixing dichloroethylaluminium with aluminium trichloride.

12. A process for dimerization or oligomerization of at least one monoolefin, comprising contacting said monoolefin with a catalytic composition produced by a process comprising contacting, in any order,
   a) at least one divalent nickel compound;
   b) at least one hydrocarbylaluminium dihalide with formula $AlRX_2$, where R is a hydrocarbyl radical containing 1 to 12 carbon atoms such as alkyl, aryl, aralkyl or cycloalkyl, and X is a chlorine or bromine atom; and
   c) at least one organic Bronsted acid;
   and preconditioning a mixture thus obtained in a solvent, at a controlled temperature and for a pre-set period, prior to its use.

13. A process according to claim 12, wherein the pre-conditioning solvent for the catalytic composition comprises a mixture of olefins with a composition analogous to that of mixtures obtained by the dimerization or oligomerization process.

14. A process according to claim 12, wherein propylene is dimerized or oligomerized, and the pre-conditioning solvent for the catalytic composition principally comprises isohexenes.

15. A process according to claim 1, wherein R is alkyl, aryl, aralkyl or cycloalkyl.

* * * * *